(12) United States Patent
Hamm et al.

(10) Patent No.: US 10,842,352 B2
(45) Date of Patent: Nov. 24, 2020

(54) ENDOSCOPE SHEATH WITH INTEGRAL IMAGING WINDOW

(71) Applicant: Canon U.S.A., Inc., Melville, NY (US)

(72) Inventors: Mark Alan Hamm, Lynnfield, MA (US); Alexander Altshuler, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 610 days.

(21) Appl. No.: 15/484,756

(22) Filed: Apr. 11, 2017

(65) Prior Publication Data
US 2017/0290492 A1 Oct. 12, 2017

Related U.S. Application Data

(60) Provisional application No. 62/320,859, filed on Apr. 11, 2016.

(51) Int. Cl.
| | |
|---|---|
| *A61B 1/00* | (2006.01) |
| *B05D 1/18* | (2006.01) |
| *B29C 41/14* | (2006.01) |
| *A61L 27/28* | (2006.01) |
| *A61B 1/005* | (2006.01) |
| *B29C 39/00* | (2006.01) |

(52) U.S. Cl.
CPC ............ *A61B 1/0011* (2013.01); *A61B 1/005* (2013.01); *A61B 1/00135* (2013.01); *A61B 1/00165* (2013.01); *B05D 1/18* (2013.01); *B29C 39/00* (2013.01); *B29C 41/14* (2013.01); *A61L 27/28* (2013.01)

(58) Field of Classification Search
CPC ... A61B 1/0011; A61B 1/00135; A61B 1/005; A61B 1/00165; A61B 1/00142; B29C 41/10; B29C 41/14; B05D 1/18; B05D 1/36; A61L 27/28
USPC ............................... 427/2.28, 2.1, 2.12, 430
See application file for complete search history.

(56) References Cited

U.S. PATENT DOCUMENTS

| | | | | |
|---|---|---|---|---|
| 4,886,049 | A * | 12/1989 | Darras | A61B 1/00142 600/124 |
| 5,337,734 | A | 8/1994 | Saab | |
| 5,347,990 | A | 9/1994 | Ebling et al. | |
| 5,463,712 | A * | 10/1995 | Cawood | A61B 1/00181 385/117 |
| 5,885,209 | A * | 3/1999 | Green | A61B 1/0011 600/104 |
| 6,030,371 | A * | 2/2000 | Pursley | A61M 25/0009 427/195 |
| 6,458,075 | B1 * | 10/2002 | Sugiyama | A61B 1/00071 600/139 |
| 6,464,632 | B1 * | 10/2002 | Taylor | A61B 1/005 138/174 |
| 8,679,002 | B2 | 3/2014 | Sutoh et al. | |
| 9,629,978 | B2 * | 4/2017 | Eversull | A61M 25/0045 |

(Continued)

*Primary Examiner* — John P Leubecker
(74) *Attorney, Agent, or Firm* — Canon U.S.A., Inc., IP Division

(57) ABSTRACT

Exemplary endoscopes, and endoscope sheaths are provided having an integrally formed imaging window. The sheath may comprise thin coiled wires and may be made using a dip-casting process. Also provided is a method which may comprise the steps of forming polymer coat(s) around a mandrel, forming a fiber assembly, forming polymer coat(s) around the fiber assembly, and forming a window around an end of the mandrel.

13 Claims, 4 Drawing Sheets

(56) References Cited

U.S. PATENT DOCUMENTS

| | | | |
|---|---|---|---|
| 2004/0068249 A1* | 4/2004 | Kampa | A61L 29/085 604/523 |
| 2005/0165366 A1* | 7/2005 | Brustad | A61B 1/0055 604/264 |
| 2006/0041187 A1* | 2/2006 | Rudischhauser | A61B 1/00163 600/138 |
| 2007/0043333 A1* | 2/2007 | Kampa | A61L 29/085 604/523 |
| 2010/0119833 A1* | 5/2010 | Madsen | A61L 27/34 428/413 |

* cited by examiner

ENDOSCOPE SHEATH WITH INTEGRAL IMAGING WINDOW

CROSS-REFERENCE TO RELATED APPLICATION(S)

This application claims priority to U.S. Provisional Application Ser. No. 62/320,859 filed Apr. 11, 2016, the content of which is incorporated herein by reference in its entirety.

BACKGROUND INFORMATION

Endoscopes are used for a variety of diagnostic and therapeutic indications. There are numerous specifically designed endoscopes including those for the examination of body parts such as the esophagus, stomach and duodenum, colon, blood vessels, bronchi, the peritoneal cavity, and joint spaces. Many of these endoscopes need a window at the distal tip of the endoscope to facilitate either viewing or molecular characterization of these tissues. For example, U.S. Pat. No. 5,347,990 describes an endoscopy having a fiber optic image bundle that can be encased in a sterile sleeve with a window at the distal end of the sleeve. Similarly, U.S. Pat. No. 8,679,002 describes an endoscopy having a fiber optic and a protective cover having a light-transmissive widow. U.S. Pat. No. 5,337,734 describes an endoscopy with a sterile cover/sheath with an optically transparent window and also provides a method of making such a sheath.

However, when the endoscope needs to be small—either to reach small or difficult to reach parts of the body or to reduce trauma, the ability to make and use endoscopes become more difficult. For example, it is difficult to form an effective imaging window while maintaining ultra-thin window and side-wall thicknesses. Similarly, the endoscope and method of making the endoscope and sheath fitting in the various components with the necessary clearances into a small outer profile is difficult. Thus, there is a need for new endoscopes, sterile sheaths, and method of making such endoscopes and sheaths.

SUMMARY OF EXEMPLARY EMBODIMENTS

According to at least one embodiment of the invention, there is provided herein a process and an endoscope and sheath having an integral window.

According to one embodiment, there is provided a process including the steps of providing a mandrel with a smooth distal end and then forming successively one or more first polymer coats around the mandrel to form a first polymer layer having a desired thickness around the mandrel. At least one optical fiber is placed along-side the first polymer layer to form a fiber assembly. One or more second polymer coats are formed around the fiber assembly to form a second polymer layer having a desired thickness around the fiber assembly. A window if formed around the distal end of the mandrel.

According to another embodiment, there is provided a process including the steps of obtaining a mandrel with a smooth distal end and inserting the mandrel with the polished end facing into an inner tube, wherein the inner tube comprises a tube portion and a wire coiled around the tube portion tube to form an assembly. The assembly is dipped into a first polymer solution having a first solvent and then flashing the first solvent off. At least one optical fiber is placed along-side the assembly to form a fiber-assembly. The fiber-assembly is dipped into a second polymer solution having a second solvent, the fiber-assembly is dried, excess second polymer solution is blown off from the distal end of the mandrel, and the second solvent is flashed off.

A number of these steps may be omitted or modified. For example, if coiled wire is not needed, the coiled wire may be omitted. In other embodiments, both the coiled wire and the inner tube are omitted, where the dip coating is used to form the endoscope sheath without any additional inner tube.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

Figure 1:
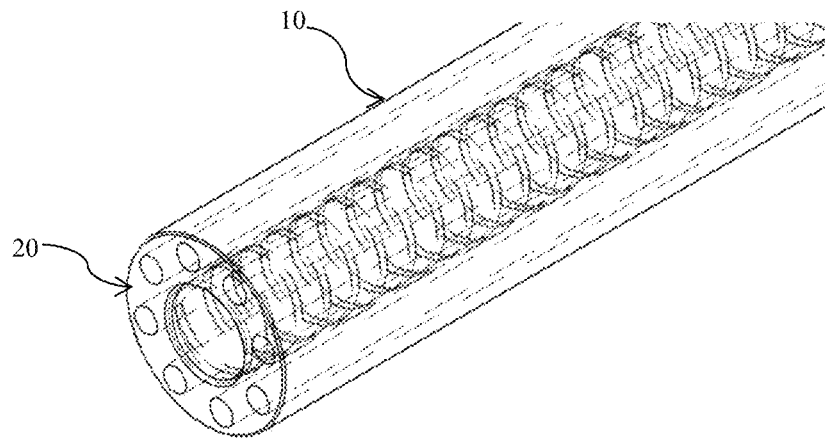
FIG. 1 is a diagram of an embodiment showing an isometric view of the distal end of a sheath of an embodiment of the invention.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

The embodiments are based on providing new sheaths, endoscopes including a sheath, and methods of making. These new apparatus and method are particularly useful when small endoscopes are required. In some embodiments, the apparatus including the sheath and endoscope is flexible, formable, and/or steerable. Additionally, the ability of the imaging core to rotate in order to form the images may be required. For example, some embodiments will provide an endoscope sheath having an outer diameter of less than 2 mm or more particularly less than 1 mm.

The imaging core and imaging system may be for, example, the imaging core and/or spectrally encoded imaging systems as described, for example, in U.S. Pat. Nos. 6,341,036; 7,447,408; 7,551,293; 7,796,270; 7,859,679; 8,045,177; 8,145,018; 8,838,213; 9,254,089; 9,295,391; 9,415,550; 9,557,154 and Patent Application Publication Nos. US2017/0035281; WO2015/116951; WO2015/116939; WO2017/024145; and U.S. Non-Provisional patent application Ser. No. 15/418,329 filed Jan. 27, 2017 each of which patents and patent publications are incorporated by reference herein in their entireties.

Figure 2:
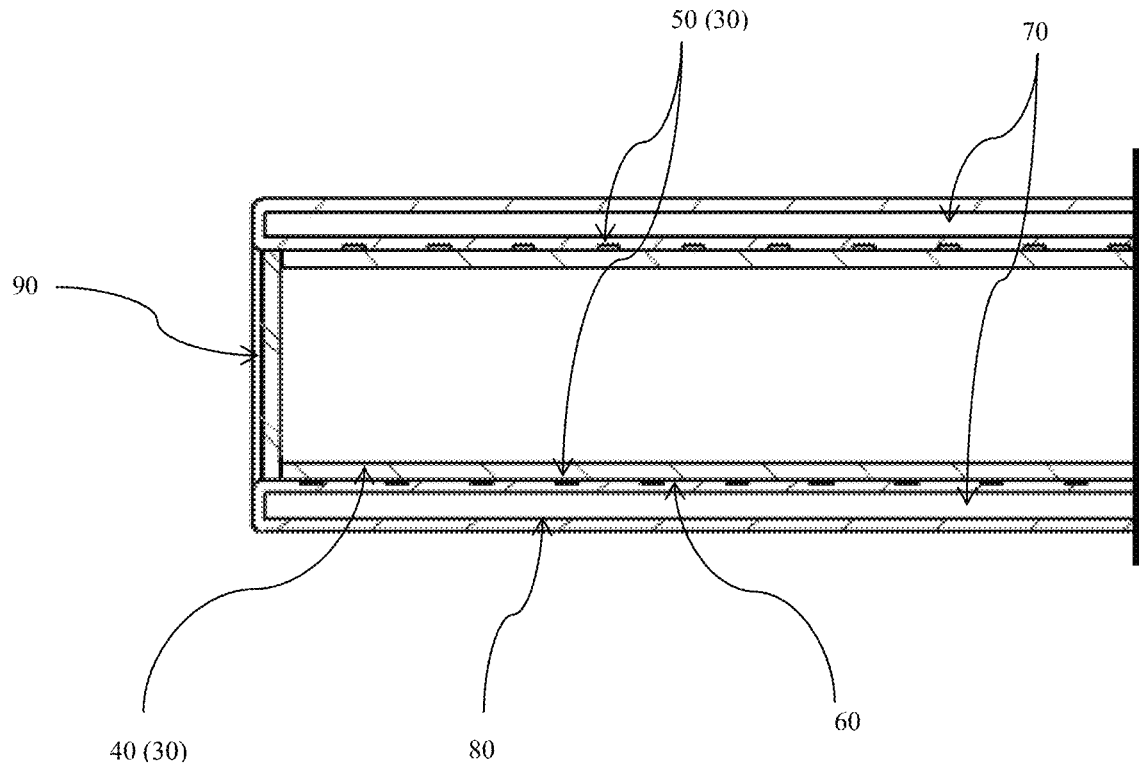
FIG. 2 is a schematic showing a sheath cross section of an embodiment of the invention.

FIG. 1 is an isometric view of a portion of a catheter sheath 10 according to an embodiment of the present invention. Particularly, the view is of a distal end 20 of the sheath. FIG. 2 is a cross-sectional view of the distal end of the sheath.

The sheath according to these embodiments is preferably thin-walled. For example, the sheath wall is less than 25 µm, or less than 100 µm or less than 50 µm, or down to about 12 µm web thickness between adjacent components that comprise the sheath. The 250 µm sheath wall thickness may include, for example, the thickness of an optical fiber and coiled flat wire within this measurement. The optical window, which may be integral in the sheath, is substantially optically clear or translucent with the wavelength range of the apparatus (e.g., between 400 and 800 nm).

The fabrication methods as provided by some embodiments as described herein, may include extrusion combined with dip-casting or just dip-casting, and/or one dip-cast component inside another dip-cast component.

Sheaths made as described herein can produce a thin-walled sheath component that allows the use of served or coiled wires within the wall. In some embodiments, the metal wires used to form the coils are particularly useful to help keep the inner diameter of the sheath substantially round and open during flexure, particularly around tight bends, a vital requirement in an imaging system that utilizes a rotating optical element positioned within the stationary sheath component, but also of value when delivering tools through the central lumen of the endoscope. The thin coiled wires also allow small diameter optical fibers to be encapsulated within the ultra-thin side-wall as well.

The material that forms the endoscope sheath is applied in thin layers via dip-casting. This provides for layers encapsulating the components that are very thin compared with, for example, web thicknesses in extrusions that require a minimum web thickness on the order of 0.0020" (50 µm). The sheath walls as presently described can be formed of layers as thin as about 0.0003" (7.5 µm), and via multiple dip and dry cycles can build up multiple layers to create the desired thickness of polymer. Through this process, an integral window covering the illumination optics (as part of or inside the assembly) and also the detection optical fibers with a window thickness on the order of 0.0010" (25 µm) may be formed. In some embodiments, the total window thickness is less than 300 µm, less than 100 µm, less than 50 µm, or less than 20 µm. In some embodiments, the thickness of the window is kept thin to reduce the potential for light from within the endoscope bore traveling through the window material and into the detection fibers located within the sheath. In some embodiments, the total window thickness is about 40-75 µm.

To form the catheter sheath such as the catheter and sheath exemplified in FIG. 1, the following steps are performed.

1. Providing a mandrel having a distal end surface with a smooth finish, such as an optically smooth finish or a mirror finish. A mandrel (not shown) is used to support forming and shaping the catheter sheath including the window surface. In one embodiment, the distal end of an appropriately sized mandrel is polished until mirror smooth. The polishing step is important when the window material without polishing is smooth or not. The polished end is intended to keep the inner window surface optically flat and transparent if window material is cast or molded using the mandrel as form. However, if the window material is a smooth film, as disclosed in U.S. Pat. No. 5,337,734, any need to finish the mandrel until it has a mirror smooth finish is not important and this step may be omitted. The polishing process is still important for embodiments that specify that there is no coating over the face of the optical detection fibers as shown in FIG. 3. In this case, the polishing operation is simply removing the coating from the face of the detection fibers, but may simultaneously polish the face(s) of the detection fibers. Similarly, other means of providing a smooth window surface may be used. When the mandrel is used to form the transparent window surface, the smoothness of the distal end of the mandrel is preferably mirror smooth. However, the amount of smoothness for the mandrel may be less than a mirror smooth finish, dependent on the requirements of the finished product. The mandrel should be appropriately sized. In some embodiments the mandrel is a polyimide tube. In some embodiments, the polyimide tube has a polytetrafluoroethylene (PTFE, or Teflon®) coating on its inner surface. The mandrel is slightly smaller than the inner dimension of the inner tube.

2. Insert mandrel with the polished end facing the distal end of an inner tube 30. The inner tube 30 may be an extruded tube, a tube formed by dip coating, etc. In some embodiments the inner tube is a polyimide tube. In some embodiments, the polyimide tube has a polytetrafluoroethylene (PTFE, or Teflon®) coating on the inner surface.

In some embodiments, the inner tube 30 includes a tube portion 40 and a wire (or wires) 50 coiled around the tube portion 40 to form an assembly. The wire or wires 50 can be wound around the outer diameter of the tube portion 40. Flat wires are particularly useful for providing crush resistance and keep the central lumen round during bending, an important attribute for imaging catheters and endoscopes that require a rotating imaging element within a stationary sheath. Flat wires also can be the simplest and most effective to coil and use. However, other wire shapes may alternatively be used, such as round, oval, etc. wires. The coiling may be a tight coil or it may be more loosely coiled around the tube portion 40. The wire 50 may be completely within the tube portion 40 or expand beyond the tube portion.

In some embodiments, an inner tube is not used and this step is omitted. Thus, the dip coating process creates the inner surface of the endoscope sheath without a prior formed tube.

3. Form a first polymer layer over the mandrel. In one embodiment, this forming step is performed by a dip casting process. The above tube-wire assembly is coated by dipping into a first polymer solution, which is a low-viscosity solvent carrying a polymer. This can be done to lock the coiled wires in place, and also to form a tacky surface onto which optical fibers can be tacked. For embodiments where an inner tube is not used, this step also creates the tube portion of the sheath. The polymer used for the first dip casting step (the first polymer solution) is for example, a polyurethane, a silicone, a butadiene-styrene, a styrene-ethylene, polyvinyl chloride, polyethylene, and mixtures of these. The polymer thus can form a translucent thin film. The solvent used can be, for example, xylene, toluene, acetone, etc.

4. Allow the solvent to flash off creating a thin layer of polymer coating. The flashing may be done at room temperature and/or pressure or at increased pressure and/or temperature. The time required for this evaporation will depend on the solvent as well as the pressure and temperature. The created thin layer of polymer coating can have a thickness of 75 μm, for example.

In some embodiments, steps 3 and 4 are repeated until the desired thickness of a first dip-cast polymer layer 60 is reached. For example, the first dip-cast polymer layer can have a thickness of 3-12 μm that is formed from the several successively created thin polymer coatings.

5. Place at least one optical fiber along-side the above assembly. This step provides optical fibers such as detection fibers 70 located around the assembly. In some embodiments, any number between 1 and 36 optical fibers (e.g., 2, 4, 6, 8, 10, 15, 16, 20, 24, or more) are placed concentrically around the assembly to create a ring of detection fibers. In some embodiments, placing the fibers means rolling the assembly over an array of fibers that are touching or particularly spaced apart. In some embodiments, the thin layer of polymer coating is sufficiently tacky to hold the at least one optical fiber in place during a second dipping process. In other embodiments, fibers are inserted into a multi-lumen extrusion.

6. Dip the assembly including the at least one optical fiber into a second polymer solution to begin forming a second thin dip-cast polymer layer. This layer may form on and around the fibers 70 and/or wires 50. The polymer used for the second dip casting step (the second polymer solution) may be the same or different from the polymer of the first polymer solution, and may be provided at the same or different concentration. Similarly, any solvent used in the first and second polymer solutions may be the same or different.

7. Remove excess second polymer solution from the distal end of the mandrel. This optional step is useful to keep the polymer layer on the end or tip uniform. This removing step can be, for example, a process of blowing or shaking off the excess droplet of solution.

8. Allow the solvent to flash off to create a thin layer of second polymer coating. The flashing may be done at room temperature and/or pressure or at increased pressure and/or temperature. The time required for this evaporation will depend on the solvent as well as the pressure and temperature.

The dipping and flashing/drying steps are then repeated until the second polymer coating 80 reaches the desired thickness. For example, the second dip-cast polymer layer 80 can have a thickness of 3-12 μm that is formed from the several successively created thin polymer coatings. The mandrel can then be removed.

This fabrication method forms a thin layer of translucent polymer over the mandrel, forming an imaging window 90 at the distal end 20, and also coats the detection fibers 70. This may or may not be desirable, so the polymer layer 80 can be polished off if the detection fibers 70 need to be exposed, or the undesirable polymer layer can simply be wiped off before the polymer dries/cures.

In some embodiments, one or more optical fibers located along-side the assembly are not required. Such embodiments may be produced by following steps 1-4 and then repeating the dipping and drying steps until the polymer coating reaches the desired thickness.

In some embodiments, steps of dipping the assembly into a polymer solution are done for the entire assembly, thus creating the entire sheath with a translucent thin film polymer.

In other embodiments, only a portion of the assembly is dip-cast. This will provide for the formation of a window in an otherwise fully dip-cast or extruded assembly. Thus, in steps 3 and 6, the dipping process occurs only to the portion on the assembly that needs to be coated with the polymer solution. In yet other embodiments, the two dipping steps may be used to dip-coat differing amounts of the assembly. For example, the first polymer coating may be done over the length of the assembly to form a tacky surface for the entire length of the assembly and the second polymer coating may coat only the window area. In another example, the first coating may encompass only the window area while the second coating encompasses the entire assembly length. In another example, different portions of the length of the endoscope may be dip-coated with various durometer materials in order to produce a sheath with varying stiffness, such as to form a soft, atraumatic tip and a stiffer proximal segment.

FIG. 2 provides a cut-away view of an exemplary catheter sheath 10 made by the process as described herein, where the inner tube, which may be an extrudate, is surrounded by a coiled flat wire 50 and then a first dip cast polymer layer 60. Detection fibers 70 and a final dip cast polymer layer 80 are shown. The distal end 20 of the sheath 10 in this view is an imaging window 90. In this embodiment, the planes of the imaging window and of the coating covering the detection fiber faces are not coincident. The planes are staggered, with an axial distance of between 0.0005" (12.7 μm) and 0.0500" (1.27 μm) to eliminate the potential problem of illumination light reflected off one or both surfaces of the window 90 entering into the detection fibers 70 which could degrade the image. The imaging window 90 thickness may range from 0.0005" (12.7 μm) to 0.0150" (380 μm), depending on the desired attributes needed. The polymer that forms the window and covers the detection fibers as well is a conformal coating, so the portion that covers the detection fibers can be staggered or stepped from the plane of the imaging window by a range of from 0.0005" (12.7 μm) to 0.050" (12550 μam), depending on the desired attributes and required performance level with respect to signal to noise ratio and field of view.

Figures 3A, 3B:
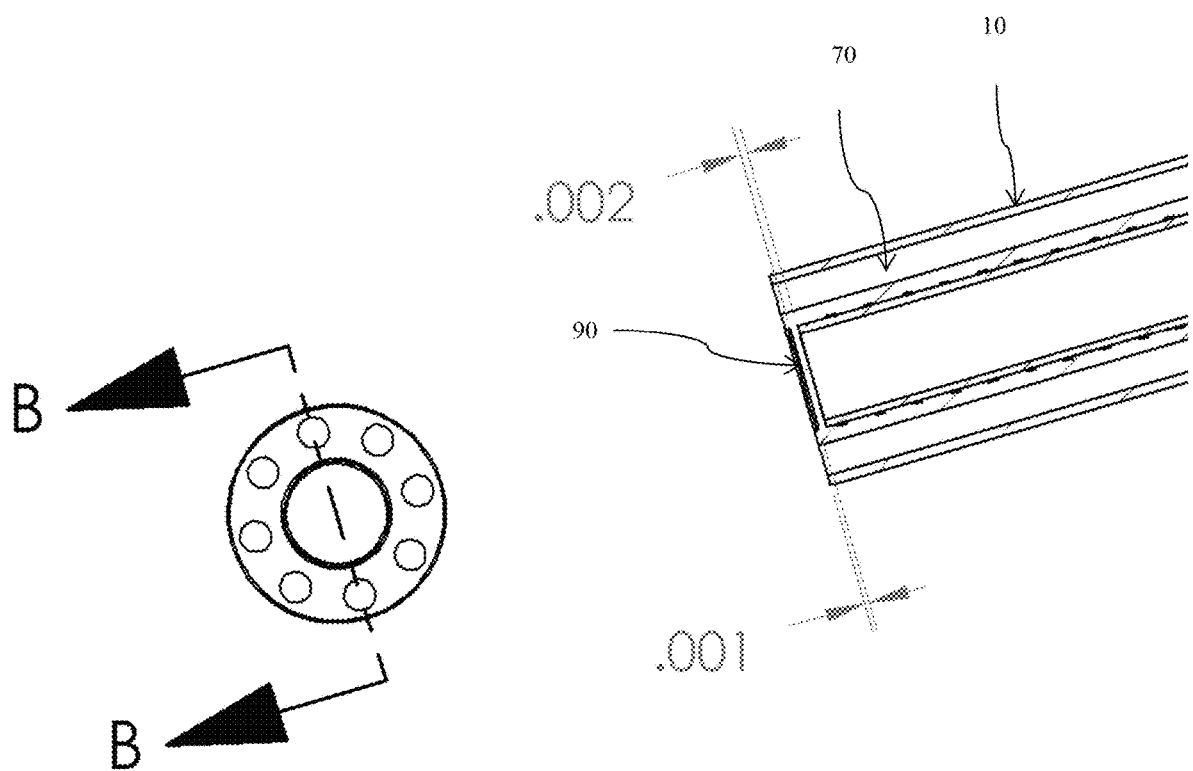
FIG. 3(A) is the schematic showing the distal end of a sheath of an embodiment of the invention.
FIG. 3(B) is a schematic showing a side view of an axial cross section of the distal end of a sheath of an embodiment of the invention.

FIG. 3(A) shows the distal end of a sheath having eight (8) optical detection fibers 70. The side view through section line "B" is shown in FIG. 3(B). As can be seen by this embodiment, the window 90 covering the central lumen of the endoscope is offset compared to the optical fibers 70 within the sheath wall. Thus, in use, where light is emitted from the core of the endoscope little to no emitted light will be able to enter the detection fiber. Thus, noise from this design is minimized.

One of the embodied fabrication methods allows the design of a catheter sheath with very thin walls with no clearance. This is an important factor in fabrication methods to keep the outer profile within the desired limits. Thin-walled tubes generally deform from an original round shape to an oval shape when bent, and if the radius of curvature is small enough the tube will kink. Whether ovalized or kinked, the inner diameter no longer affords the imaging core to rotate freely, and image distortion called Non-Uniform Rotation Distortion (NURD) will likely occur.

Thin walls are also important to isolate adjacent components within the sheath wall, such as the optical fibers 70 and the metallic coil winds 50. Another example is isolating the rotating, imaging core (not shown for clarity) from the metallic winds of the served wire coil. Conventional extrusion techniques require a minimum wall thickness of around 0.0020" (50 µm), where a typical dip-cast wall thickness may be significantly less.

The combination of properties needed requires thinner wall thicknesses than are feasible with extrusion techniques to create a sheath that is flexible, possibly formable into a tight radius, and possibly steerable while keeping the inner diameter open and round to facilitate distortion-free images and also keeping the profile low.

In some embodiments, the coiled wire 50 is a flat stainless steel wire with dimensions on the order of 0.0005"×0.0025" that is coiled around the inner tube 40 (or the first dip-cast polymer layer) 60 to keep the inner diameter round during bending, while the 0.0005" radial thickness lends itself to keeping the profile and wall thickness small while providing enough radial stiffness to be effective.

In some embodiments, the optical fibers 70 selected are in the range of 0.0020" to 0.0095" (50 µm to 250 µm) diameter. Again, this is to keep the outer profile as small as possible. Thus, in other embodiments where the overall size may be larger, larger diameter optical fibers may be used. In yet other embodiments, the optical fibers may surround the inner tube in multiple layers. These layers may be formed at one time, or an additional dip casting step can be included after the first layer of optical fibers are placed on the assembly.

In another embodiment, the dip-cast material that covers the detection fibers 70 is polished off. This may be done in the same polishing operation that is required to polish the face of the detection fibers, or alternatively just to expose the fiber faces that are already polished or cleaved.

In some embodiments, an alternate method of fabrication is used. This method employs conventional extrusion methods to extrude a multi-lumen extrusion that is larger than the final probe profile needed to meet the needs of the intended users. The large extrusion is then necked or drawn down to final size using heat and tension, shrink tube, or a drawing die, after certain components have been inserted into the larger profile extrusion. This method allows the extruder to manufacture the original, larger diameter tubing with thicker wall thicknesses and more generous tolerances, which makes the extrusion easier to fabricate and keeps costs down. The components are fixed into the distal end of the larger extrusion, and then the extrusion is necked, stretched or drawn down, possibly through a die that serves to set the final outer diameter of the probe. In some cases it may be desirable to use both a heat shrink tube and a drawing die to better control the outer diameter, surface finish and profile of the sheath. This process also reduces the inner diameters of the extrusion, while reducing or eliminating required clearances needed to insert the components. This process may require an appropriately sized mandrel to set and maintain the inner lumen diameter, which must be sized appropriately to attain proper function with respect to imaging parameters and particularly NURD.

In one embodiment, only the distal end of the larger extrusion is drawn down to the final diameter. The original-size extrusion with larger diameters and wall thicknesses is useful to form the proximal portion of the device which does not enter into the anatomy, and is attached to the handle to provide the user with better control of the device. The handle may be used, for example, to facilitate ease of use in various lumens and spaces within the anatomy including ENT, GI, URO, mucous membranes, and bronchial tubes.

In yet other embodiments, the detection fiber faces are left exposed and not coated with polymer to maximize the amount of light collected by these detection optical fibers and to minimize the amount of illumination light from the imaging core that enters the detection fibers.

Figure 4A:
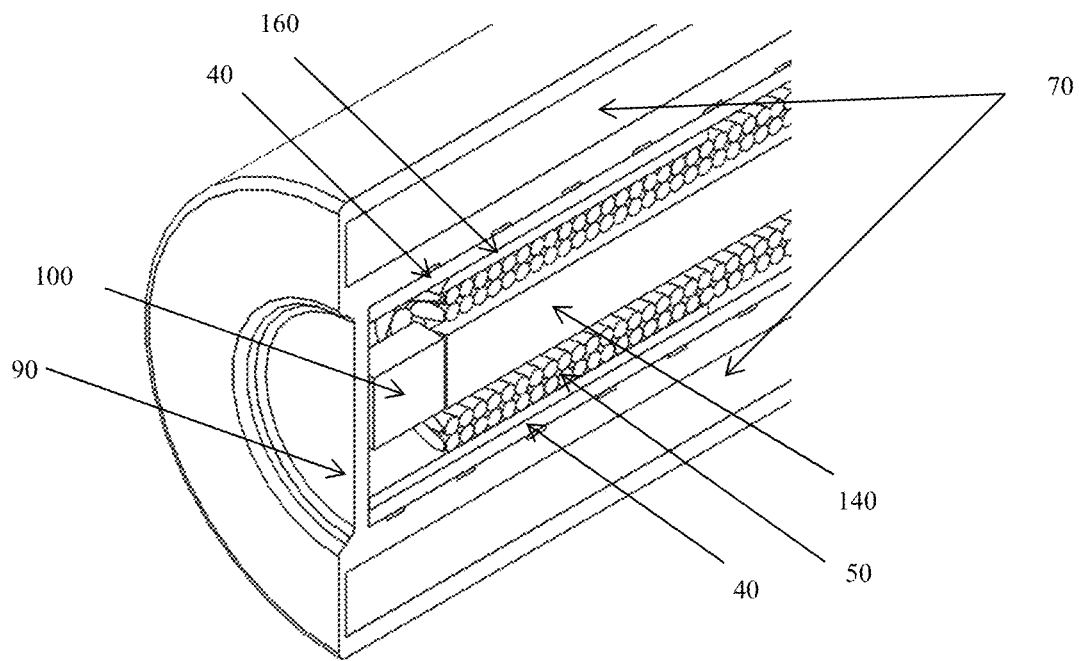
FIG. 4(A) is a schematic showing the distal end of endoscope, isometric view. This is an axial cross section of an exemplary probe tip including imaging core assembly and angle-cut PTFE tube.
Figure 4B:
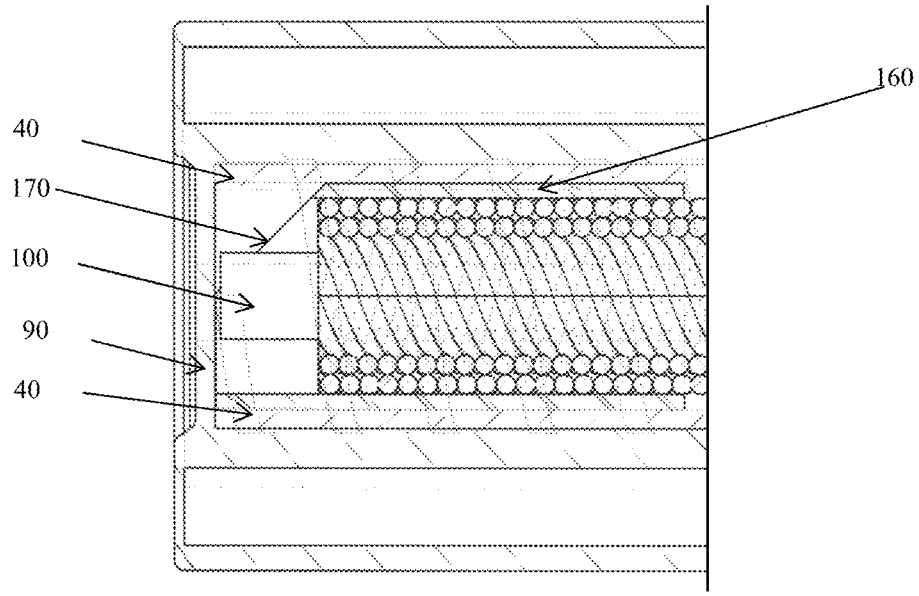
FIG. 4(B) is a schematic showing the distal end of endoscope, side view, axial cross section including imaging core assembly and angle-cut PTFE tube of a sheath of an embodiment of the invention.

In some preferred embodiments, as exemplified in FIGS. 4(A) and 4(B), a tubing such as a PTFE or FEP tubing or heat shrinkable tubing 160 is attached to the imaging core 140 and positioned over the distal optics 100. Since the imaging core 140 may need to rotate during use, the low-friction PTFE tubing 160 is held in contact with the imaging window 90 during rotational imaging to accurately position the distal optics 100 in close proximity to the imaging window 90 to provide the widest possible field of view. The distal optics 100 are positioned appropriately within the PTFE tubing 160 at manufacturing so as to keep the optics very close, but not touching the imaging window because they could be damaged if the come in contact with the imaging window. An angled front surface 170 of the tubing 160 may be used as shown in FIG. 4(B). The distal tip of PTFE tube 160 is angle-cut forming angled from surface 170 to allow illumination light to pass without restriction from PTFE tube 160, which might limit the field of view if it were not angle cut.

In preferred embodiments that include an imaging window 90 that is integral to the native material of the sheath, the mandrel (not shown) must have a smooth distal end, for example, the distal end of the mandrel is polished prior to use. Preferably, the polished mandrel is polished to an optically smooth surface, or a surface quality of 10-20, which specifies that the window surface is flat and smooth within the illumination wavelength divided by 8. This is to ensure that the imaging window surface is held flat and smooth during heating above the melt temperature during the melt-bonding process that is utilized to attach an inserted window that is the same material as that used to form the sheath itself to the sheath material, forming an integrated window sheath.

Figures 5A, 5B:
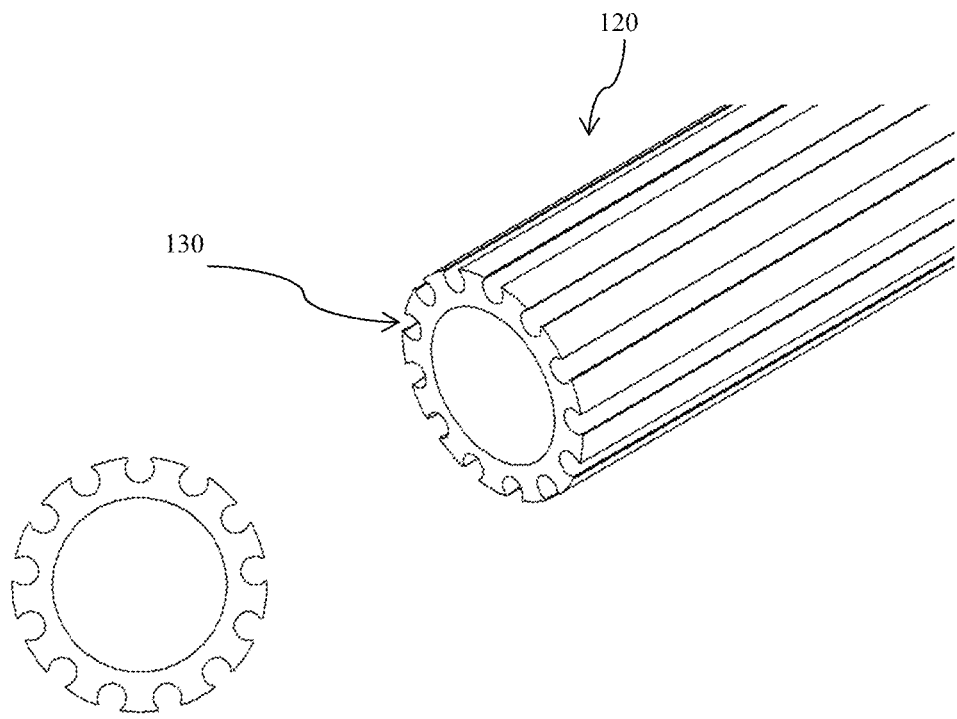
FIGS. 5(A) and 5(B) are schematic views of an extrusion component of an embodiment of the present invention shown from the distal end (FIG. 5(A)) and an isometric view (FIG. 5(B)).

Other embodiments utilize an extrusion 120 as shown in FIGS. 5A and 5B to facilitate the task of inserting fibers into long lumens. The extrusion allows the detection fibers to be inserted from the side rather that inserted from the end and pushed/pulled through a lumen. The fibers are pushed into the fiber slots 130 disposed longitudinally along the outer diameter of the extrusion. Thus, when this extrusion is used, the first several steps as described above are not required. After the optical fibers are pushed into the fiber slots, the assembly is then dip coated in the second polymer or alternatively the material from the native extrusion is reflowed with a heat shrinkable tube to form a smooth outer surface. Another alternative fabrication method is to cover extrusion 120 with a separate tube such as heat shrink tube that is left in place to cover extrusion 120 along with the optical fibers disposed within fiber slots 130.

In some embodiments, a window element (not shown) is inserted into the sheath as the imaging window. This insertable imaging window is attached at the distal end of the central lumen. This window element can be formed form common, optically clear materials such as glass, silica, sapphire, quartz, etc. Instead of completely forming the imaging window through dip coating, this premade window can be formed as an optically flat material or similar and secured at the distal end of the endoscope.

In another embodiment, a cylinder of PEBAX® is inserted into the drawn-down sheath assembly comprising a PEBAX® multilumen extrusion, glass detection optical fibers and a PTFE-lined polyimide tube that includes a served or coiled metallic wire. Since this inserted cylinder is an identical material that the multilumen extrusion is fabricated from, the cylinder can be melt-bonded to the native PEBAX® material of the multilumen extrusion, thusly forming an integral window. In this case, the inner surface of the PEBAX® cylinder is optically smooth, and is forced against the mirror-smooth face of the mandrel during heating to maintain the optically smooth surface quality. The operation of adding the PEBAX® window to the PEBAX® multilumen sheath utilizes heat shrinkable tubing and a coated mandrel to constrain the outer diameter and inner diameters of the multilumen extrusion while heated above the melting temperature of PEBAX® to melt-bond the PEBAX® window to the PEBAX® multilumen extrusion that forms the sheath. The outer surface of the PEBAX window is then polished to set the final thickness, and to form an optically smooth finish on the outer surface of the window.

In another embodiment, the cylindrical PEBAX® window is bonded in place using an adhesive, thusly maintaining the optically smooth inner surface. After bonding, the outer surface of the window is then polished as said above.

Figure 6:
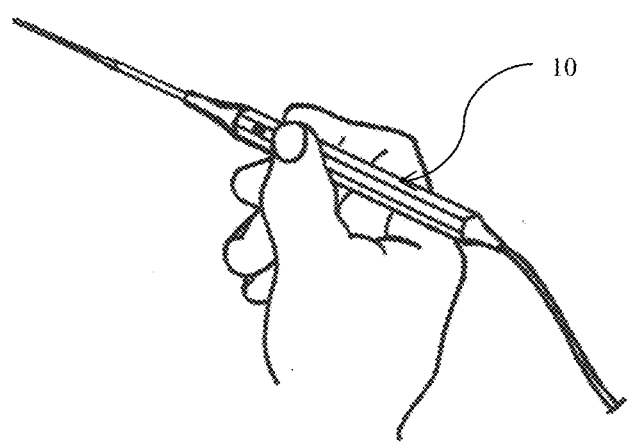
FIG. 6 shows an endoscope containing the probe of an embodiment of the present invention held and ready for use.

Thus, in use, as shown in FIG. 6, the catheter sheath

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A process comprising:
   providing a mandrel with a smooth distal end;
   forming successively one or more first polymer coats around the mandrel to form a first polymer layer having a desired thickness around the mandrel;
   placing at least one optical fiber along-side the first polymer layer to form a fiber assembly;
   forming successively one or more second polymer coats around the fiber assembly to form a second polymer layer having a desired thickness around the fiber assembly; and
   forming a window around the distal end of the mandrel;
   wherein the step of forming the successively one or more first polymer coats includes:
   dipping the mandrel into a first polymer solution containing a first solvent and a first polymer material; and
   flashing the first solvent off to form the first polymer coat made of the first polymer material.

2. A process comprising:
   providing a mandrel with a smooth distal end;
   inserting the mandrel with the smooth distal end facing into a tube;
   forming successively one or more first polymer coats around the mandrel to form a first polymer layer having a desired thickness around the mandrel;
   placing at least one optical fiber along-side the first polymer layer to form a fiber assembly;
   forming successively one or more second polymer coats around the fiber assembly to form a second polymer layer having a desired thickness around the fiber assembly;
   forming a window around the distal end of the mandrel;
   wherein in the step of forming the one or more first polymer coats, the one or more first polymer coats are formed around the tube having the mandrel inserted therein.

3. The process according to claim 2, wherein a wire is coiled around the tube, and
wherein in the step of forming the one or more first polymer coats, the one or more first polymer coats are formed around the tube having the coiled wire.

4. A process comprising:
providing a mandrel with a smooth distal end;
forming successively one or more first polymer coats around the mandrel to form a first polymer layer having a desired thickness around the mandrel;
placing at least one optical fiber along-side the first polymer layer to form a fiber assembly;
forming successively one or more second polymer coats around the fiber assembly to form a second polymer layer having a desired thickness around the fiber assembly; and
forming a window around the distal end of the mandrel;
wherein the step of forming the window includes forming one or both of the first and second polymer layers around the smooth distal end of the mandrel.

5. The process according to claim 4, wherein the window is formed such that a plane of the window and a face plane of at least one optical fiber are not coincident.

6. The process according to claim 4, wherein the window is formed such that a plane of the window and a face plane of at least one optical fiber are staggered.

7. A process comprising:
obtaining a mandrel with a smooth distal end;
inserting the mandrel with the smooth distal end facing into an inner tube, wherein the inner tube comprises a tube portion and a wire coiled around the tube portion tube to form an assembly;
dipping the assembly into a first polymer solution having a first solvent;
flashing the first solvent off;
placing at least one optical fiber along-side the assembly to form a fiber-assembly;
dipping the fiber-assembly into a second polymer solution having a second solvent;
drying the fiber-assembly;
blowing off excess second polymer solution from the distal end of the mandrel; and
flashing off the second solvent.

8. The process of claim 7, wherein the steps of dipping the fiber-assembly into the second polymer solution, drying, blowing off the excess second polymer solution, and flashing the first and second solvents are repeated until a first polymer coating layer and a second polymer coating layer reach desired thicknesses.

9. The process of claim 7, wherein the steps of dipping the assembly into a first polymer solution and flashing off the first and second solvents are repeated a plurality of times.

10. The process of claim 7, wherein the first polymer solution is selected for its ability to form a tacky surface onto which the at least one optical fiber can be tacked.

11. The process of claim 7, wherein the assembly is dipped to form a sheath for endoscopic use.

12. The process of claim 7, wherein the assembly is dipped such that only a portion of the assembly forms a dip-cast.

13. The process of claim 7, wherein the inner tube is an extruded material.

* * * * *